United States Patent [19]
Adams et al.

[11] Patent Number: 5,941,871
[45] Date of Patent: Aug. 24, 1999

[54] CATHETER SYSTEMS WITH INTERCHANGEABLE PARTS

[75] Inventors: Daniel O. Adams, Long Lake; Roger Hastings, Maple Grove; Louis Ellis, St. Anthony, all of Minn.

[73] Assignee: SciMed Life Systems, Inc., Maple Grove, Mich.

[21] Appl. No.: 09/045,390

[22] Filed: Mar. 20, 1998

Related U.S. Application Data

[62] Division of application No. 08/748,771, Nov. 14, 1996, Pat. No. 5,730,734.

[51] Int. Cl.$^6$ .................................................. A61M 25/00
[52] U.S. Cl. ........................................ 604/523; 604/539
[58] Field of Search ................................. 604/523, 524, 604/526, 527, 532, 533, 539, 96, 500, 508, 509, 264; 606/192–194

[56] References Cited

U.S. PATENT DOCUMENTS

| | | | |
|---|---|---|---|
| 4,085,757 | 4/1978 | Pevsner | 128/325 |
| 4,311,146 | 1/1982 | Wonder | 128/325 |
| 4,327,734 | 5/1982 | White, Jr. | 128/325 |
| 4,341,218 | 7/1982 | U | 128/325 |
| 4,364,392 | 12/1982 | Strother et al. | 128/325 |
| 4,395,806 | 8/1983 | Wonder et al. | 29/157.1 A |
| 4,401,433 | 8/1983 | Luther | 604/159 |
| 4,413,989 | 11/1983 | Schjeldahl et al. | 604/96 |
| 4,517,979 | 5/1985 | Pecenka | 128/325 |
| 4,545,367 | 10/1985 | Tucci | 128/1 R |
| 4,820,271 | 4/1989 | Deutsch | 604/99 |
| 4,927,413 | 5/1990 | Hess | 604/95 |
| 4,976,697 | 12/1990 | Walder et al. | 604/164 |
| 5,045,061 | 9/1991 | Seifert et al. | 604/96 |
| 5,084,010 | 1/1992 | Plaia et al. | 604/22 |
| 5,100,381 | 3/1992 | Burns | 604/96 |
| 5,117,831 | 6/1992 | Jang et al. | 128/662.06 |
| 5,154,725 | 10/1992 | Leopold | 606/194 |
| 5,158,548 | 10/1992 | Lau et al. | 604/96 |
| 5,181,921 | 1/1993 | Makita et al. | 606/195 |
| 5,217,482 | 6/1993 | Keith | 606/194 |
| 5,236,424 | 8/1993 | Imran | 604/280 |
| 5,267,982 | 12/1993 | Sylvanowicz | 604/281 |
| 5,304,123 | 4/1994 | Atala et al. | 604/54 |
| 5,330,466 | 7/1994 | Imran | 606/13 |
| 5,333,609 | 8/1994 | Bedingham et al. | 128/632 |
| 5,334,148 | 8/1994 | Martin | 604/96 |
| 5,338,300 | 8/1994 | Cox | 604/96 |
| 5,358,493 | 10/1994 | Schweich, Jr. et al. | 604/264 |
| 5,368,564 | 11/1994 | Savage | 604/95 |
| 5,378,236 | 1/1995 | Seifert | 604/96 |
| 5,383,923 | 1/1995 | Webster, Jr. | 607/125 |
| 5,385,562 | 1/1995 | Adams et al. | 604/280 |
| 5,399,164 | 3/1995 | Snoke et al. | 604/95 |
| 5,403,274 | 4/1995 | Cannon | 604/9 |
| 5,411,475 | 5/1995 | Atala et al. | 604/54 |
| 5,477,856 | 12/1995 | Lundquist | 128/642 |
| 5,490,837 | 2/1996 | Blaeser et al. | 604/96 |
| 5,545,136 | 8/1996 | Berger | 604/96 |
| 5,549,554 | 8/1996 | Miraki | 604/101 |
| 5,632,754 | 5/1997 | Farley et al. | 606/159 |
| 5,730,734 | 3/1998 | Adams et al. | 604/280 |

FOREIGN PATENT DOCUMENTS

| | | |
|---|---|---|
| 0 277 366 A1 | 8/1988 | European Pat. Off. . |
| 0 380 227 A2 | 8/1990 | European Pat. Off. . |
| WO 96/00099 | 1/1996 | WIPO . |
| WO 96/23542 | 8/1996 | WIPO . |

*Primary Examiner*—John D. Yasko
*Attorney, Agent, or Firm*—Crompton, Seager & Tufte, LLC

[57] ABSTRACT

A catheter system having a changeable distal member. The catheter system includes a proximal member, including a shaft having a proximal end, a distal end and a lumen extending therethrough. A distal member is included having a distal portion which may be passed through the lumen of the proximal member and releasably sealed to the proximal member at a desired location during a catheter procedure. The distal member may further include a push member operably coupled to the distal portion. The distal member may include a fluid-tight releasable seal for releasably sealing the distal member to the proximal member.

17 Claims, 8 Drawing Sheets

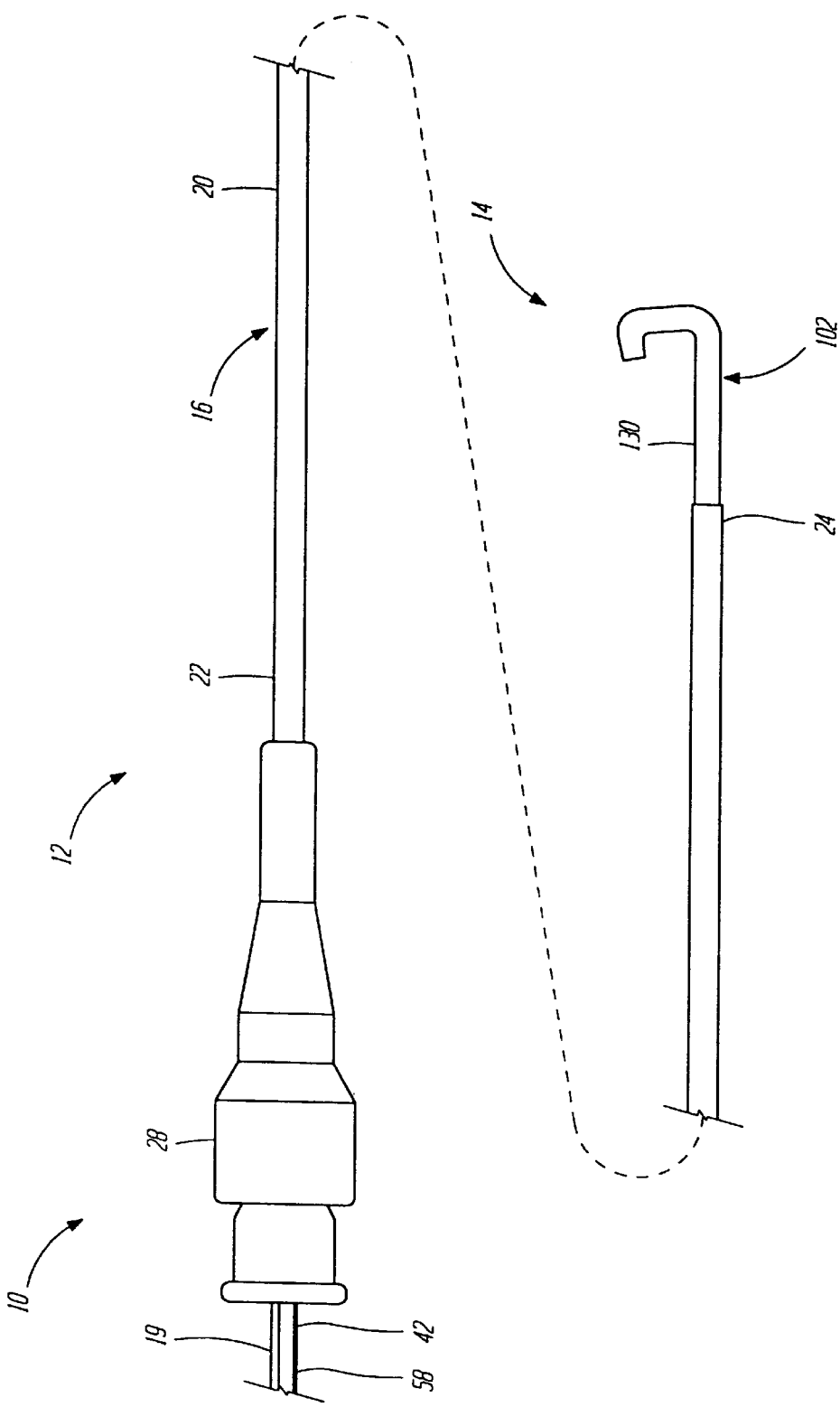

great CATHETER SYSTEMS WITH
INTERCHANGEABLE PARTS

This application is a divisional of U.S. application Ser. No. 08/748,771, filed Nov. 14, 1996, now U.S. Pat. No. 5,730,734 entitled "CATHETER SYSTEMS WITH INTERCHANGEABLE PARTS".

FIELD OF THE INVENTION

The present invention generally relates to intravascular devices with interchangeable parts. More particularly, the present invention relates to intravascular catheters such as angioplasty catheters and guide catheters with anatomically-specific interchangeable parts.

BACKGROUND OF THE INVENTION

Intravascular diseases are commonly treated by relatively non-invasive techniques such as percutaneous translumenal coronary angioplasty (PTCA). PTCA is well known in the art and typically involves the use of a guide catheter, a guide wire and a balloon catheter, possibly in combination with other intravascular devices. A typical balloon catheter has an elongate shaft with a balloon attached proximate its distal end and an inflation manifold attached proximate the proximal end. In use, the balloon catheter is advanced through a lumen in the guide catheter over the guide wire such that the balloon is positioned adjacent a restriction in a diseased vessel. The balloon is then inflated and the restriction in the vessel is opened.

PTCA devices come is a variety of shapes and sizes depending on the nature of the anatomy in which the device will be used. For example, a PTCA procedure may be performed in either the right or left coronary arteries, each requiring a guide catheter having a different shape on the distal end to track the vessel anatomy. In addition, a PTCA procedure may be performed in either (or both) a proximal or distal portion of each of the coronary arteries, each requiring a different sized balloon catheter. Furthermore, there are anatomical differences between patients which may require a different shaped or sized intravascular device for treatment.

To meet the above cited needs, guide catheters and balloon catheters are manufactured in various sizes and shapes as a total unit which is used once and discarded. However, often only a portion of each device is of different size or shape. For example, only the distal portion of a guide catheter varies in shape depending on the given anatomical geometry to be navigated while the proximal portion of the guide catheter is of the same size and is almost always a straight tubular member. Accordingly, it would be desirable to have a guide catheter with a standard proximal portion and an interchangeable distal portion. Likewise, it would be desirable to have other intravascular devices with interchangeable parts so that the portion of the device which does not have to change size or shape can be used with multiple interchangeable portions. By using a standard portion in conjunction with multiple interchangeable portions, hospital inventories can be reduced, manufacturing costs can be reduced, and unnecessary waste can be eliminated.

With present intravascular devices, when it becomes necessary to change to a device having a different size or shape in the distal portion, it is necessary to remove the entire device from the vascular system of the patient and replace such device with the new device. In general, this requires pulling the entire device back through the vasculature, out the point of insertion at such location as the femoral artery, and reinserting an entirely new device by threading such device over the guide wire up to the treatment site. This increases the overall treatment time when it is necessary to use devices of different size or shape in the procedure. Therefore, it would be desirable to have an intravascular device with a single proximal portion which is standardized to be utilized with multiple interchangeable distal portions which can be changed to the desired distal portion during an intravascular procedure without removing the standardized proximal portion from the patient.

SUMMARY OF THE INVENTION

The present invention overcomes the disadvantages of the prior art and provides a catheter system having interchangeable parts. In one embodiment, the present invention includes a catheter system having a changeable distal portion.

The present invention includes a proximal portion and a distal portion. The proximal portion may include a shaft having a lumen extending therethrough, with the distal portion being insertable within the proximal shaft lumen. A seal member is provided coupled to the distal portion for providing a fluid-tight releasable seal between the proximal portion and the distal portion at a desired location along the length of the proximal portion shaft. The distal portion may be changed to a different distal portion during an intravascular procedure without removing the standardized proximal portion from the patient.

The distal portion includes a push member having a proximal end and a distal end, wherein the distal end is operably coupled to the distal portion. A seal may be located proximate the proximal end of the distal portion for releasably sealing the distal portion to the proximal portion. The distal portion may be a balloon catheter assembly. The balloon catheter assembly may include a dilatation balloon coupled to a proximal extension having the seal member mounted thereon. The catheter assembly may be a single lumen or dual lumen design.

The fluid-tight seal allows fluid communication between the proximal shaft lumen and the balloon for inflation/deflation of the balloon. The seal may be an interference type seal, such as an O-ring seal. The seal may be an alternative type seal, such as a collar, bladder, or valve type seal.

A distal seal may be coupled to the balloon catheter. The distal seal may be located proximate a distal end of the balloon. The distal seal provides a fluid-tight releasable seal to a device passing therethrough, such as a guide wire. The distal seal may be an O-ring type seal.

The catheter system may include a balloon shaft extending proximal of the balloon, having the seal mounted thereon. The catheter system may further include a balloon support member extending from the balloon shaft to a distal end of the balloon. The distal seal may be coupled to the balloon support member. The balloon support member may be a tubular member. Alternatively, the balloon support member may be a rod or other push member transmitting pushing force to the distal end of the balloon.

The catheter system in accordance with the present invention allows for use of a smaller guide catheter with the dilatation balloon system. Further, the catheter system in accordance with the present invention may be used as a rapid exchange catheter or a solo operator exchange catheter system.

Alternatively, the distal portion may be a guide member, including a distal guide catheter portion which may be passed through the proximal portion shaft lumen and releasably sealed to the proximal portion at a desired location during a catheter procedure. The distal guide catheter portion may be shaped or curved to accommodate various anatomical features. The guide member may further comprise a push member operably coupled to the distal guide catheter portion. The catheter system may further comprise a guide member seal extending from the distal guide catheter portion for providing a releasable fluid-tight seal between the guide member and the proximal portion.

BRIEF DESCRIPTION OF THE DRAWINGS

FIG. 1D is a partial longitudinal sectional view of another embodiment of the changeable distal portion of the catheter system in accordance with the present invention taken along line 1D—1D of FIG. 1;

FIG. 2 is a side view of another embodiment of a catheter system having a changeable distal portion in accordance with the present invention;

DETAILED DESCRIPTION OF THE PREFERRED EMBODIMENTS

The presently preferred embodiments and methodology described herein are applicable to intravascular procedures and are specifically described in the context of coronary dilatation balloon and guide catheters. It should be understood, however, that the embodiments and methodology of the present invention may be adapted for use with other types of intravascular devices, such as atherectomy, diagnostic, and ultrasonic catheters.

Figure 1:
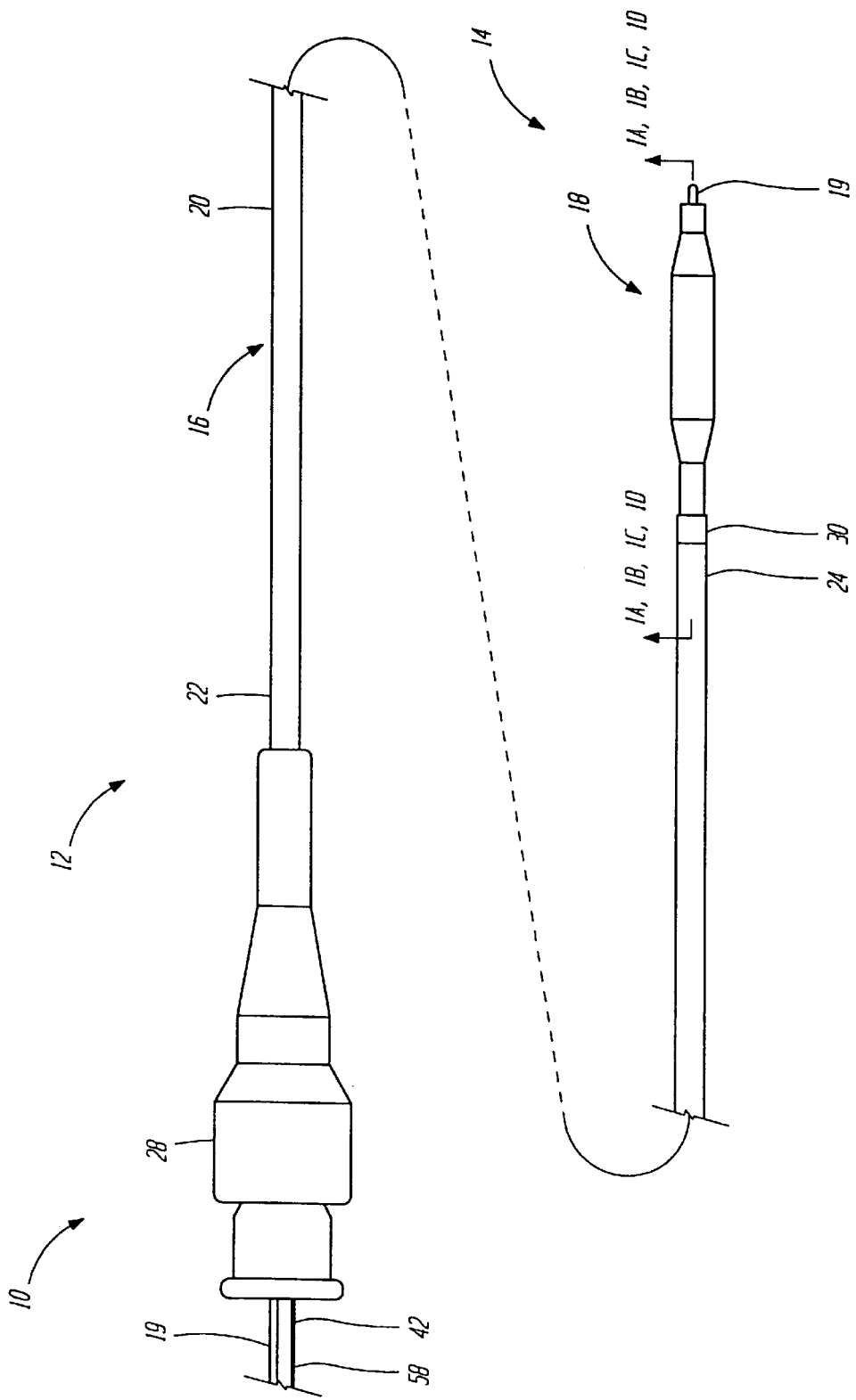
FIG. 1 is a side elevational view of one embodiment of a catheter system having a changeable distal portion in accordance with the present invention.

Referring to FIG. 1, a catheter assembly in accordance with the present invention is shown generally at 10. The catheter assembly 10 generally includes a proximal catheter portion 12 and a changeable distal catheter portion 14. The changeable distal catheter portion 14 may be releasably engaged/coupled to the proximal catheter portion 12, and may be exchanged during a catheter procedure. The catheter assembly 10 may be inserted within a guide catheter during a catheter procedure.

In one preferred embodiment, the proximal catheter portion 12 is a tubular sheath or guide catheter 16 and the distal catheter portion 14 is a dilatation balloon assembly 18. The guide catheter 16 is positioned over a portion of the dilatation balloon assembly 18. The dilatation balloon assembly 18 is shown extending from the guide catheter 16, and positioned over a guide wire 19.

Guide catheter 16 includes a shaft 20 having a proximal end 22 and a distal end 24. A shaft lumen 26 (shown in FIG. 1A) extends longitudinally through the shaft 20 from the proximal end 22 to the distal end 24. Operably connected to the proximal end 22 is a catheter manifold/hub assembly 28 which communicates with lumen 26 for connection to ancillary devices (not shown) for controlling the passage of fluids and devices therethrough. Located at the distal end 24 of the shaft 20 is a soft tip 30. Soft tip 30 provides for atraumatic engagement of the ostium of the coronary artery receiving treatment.

In one embodiment, the guide catheter shaft 20 is formed from an extrusion process, which may include a single or multi-layered design (not shown). In one preferred embodiment, the shaft 20 is formed from a multi-layered construction which includes a first inner layer for decreasing the co-efficient of friction within lumen 26 for passing treatment devices therethrough, and a second outer layer for stable positioning of the guide catheter shaft 20 and providing backout support during other treatment procedures. The first inner layer may be formed of polytetrafluoroethylene and may further include a hydrophilic coating, and the outer layer may be commonly formed of polyethylene, polyurethane, polyether block amide, nylon, or a blend of these. Shaft 20 may further include a third intermediate layer positioned between the first inner layer and the second outer layer formed of a braided construction for providing kink-resistance and torque control to the guide catheter 16.

The distal catheter portion 14 is resealably connected to the proximal catheter portion 12, allowing for balloon inflation/deflation and easy exchange of the distal catheter portion 18 during a catheter procedure without removing the proximal catheter portion from the patient. Further, the proximal catheter portion 12 may be resterilized and reused, with other distal catheter portions 14.

Figure 1A:
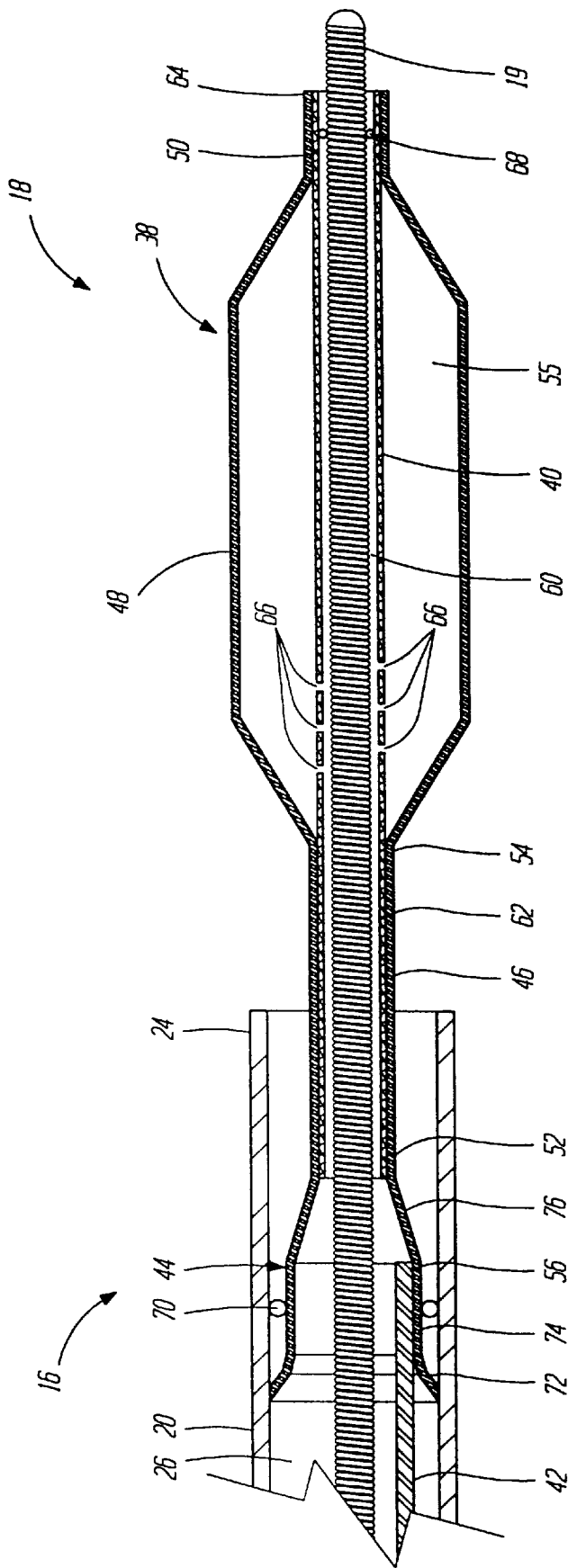
FIG. 1A is a partial longitudinal sectional view showing the changeable distal portion of the catheter system in accordance with the present invention taken along line 1A—1A of FIG. 1.

Referring to FIG. 1A, a longitudinal cross section of dilatation balloon assembly 18 extending from guide catheter 16 is shown. In a first embodiment, the dilatation balloon assembly 18 generally includes a dilatation balloon system 38, a support member 40, and a push member 42. In the embodiment shown, the support member 40 is a tubular shaft and the push member 42 is a core wire. It is also recognized that push member 42 may be a thin walled tube or a flat convex ribbon (such as part of a tube).

The dilatation balloon system 38 is in fluid communication with guide catheter 16. The dilatation balloon system 38 includes a proximal extension member 44, a proximal shaft or neck portion 46, balloon 48, and distal neck portion 50. Proximal extension member 44 extends from a proximal end 52 of proximal neck portion 46. Alternatively, it is recognized that proximal extension member 44 may be a separately formed tubular member extending from the balloon 48. Balloon 48 extends from a distal end 54 of proximal neck portion 46. It is recognized that proximal neck portion 46 may be a relatively short segment, or proximal neck portion 46 may be a relatively long segment as desired for a specific anatomical procedure. The proximal extension member 44 and proximal neck portion 46 may be formed of a polymeric material. For example, in one embodiment, the proximal extension member 44 and proximal neck portion 46 are formed of a suitable medical grade polymer, such as HDPE, polyether block amide, or a polyolefin copolymer.

Balloon 48 has an interior balloon chamber 55. The balloon 48 can be formed of a polyolefin copolymer or other polymer material. For example, in one embodiment, the balloon 48 is formed of a polyolefin copolymer (such as sold by DuPont under the tradename SURLYN as Resin No. 8527) or polyethylene terephthalate, polyethylene, polyvinylchloride, or ethylene vinyl acetate. The distal neck portion 50 extends from an opposite end of balloon 48.

Push member 42 is operably coupled to dilatation balloon system 38. Push member 42 includes a push member distal end 56 and a push member proximal end 58. The push member distal end 56 is coupled to the interior wall of proximal extension member 44. For example, in one embodiment, the push member distal end 56 is bonded to the proximal extension member 44 using an adhesive. The push member 42 extends through the lumen 26 of guide catheter 16, with the push member proximal end 58 exiting the hub assembly 28. Push member 42 provides movement and control of the dilatation balloon system 38 relative to guide catheter 16 from a location proximal of the hub assembly 28, while the catheter assembly 10 is positioned within a patient's vascular system.

Support member 40 includes an interior chamber 60, and extends through the balloon 48 between the proximal neck portion 46 and the distal neck portion 50. In the embodiment shown, support member 40 is formed of a polymeric material, and is stiff enough to provide longitudinal support to balloon 48. Support member 40 includes a shaft proximal portion 62 sealed to the interior of proximal neck portion 46, and a shaft distal portion 64 sealed to the interior of distal neck portion 50. Interior chamber 60 (at the support member proximal portion 62) is in fluid communication with the guide catheter lumen 26. Support member openings 66 are located along the support member 40, allowing inflation fluid for inflation/deflation of balloon 48 to pass between interior chamber 60 and balloon chamber 55.

Located at the support member distal portion 64 is distal seal member 68. The distal seal member 68 is located about the interior chamber 60 of support member 40. The distal seal member 68 allows movement of guide wire 19 relative to support member 40, while inhibiting inflation fluid from exiting the support member 40.

In a first embodiment, the distal seal member 68 is an O-ring seal formed of a soft, polymeric material. The distal seal member 68 extends about the entire interior periphery of interior chamber 60. Preferably, the outer diameter of guide wire 19 is proximate the inner diameter of distal seal member 68 to create an interference fit which allows slidable movement of the guide wire 19 relative to the seal member 68. When balloon 48 is inflated with fluid, the interference seal between the distal seal member 68 and the guide wire 19 inhibits inflation fluid from exiting the balloon 48 through support member 40. It is recognized that guidewire 19 may be a coil guidewire (as shown) or a solid guidewire. In other embodiments, it is recognized that distal seal member 68 may be an alternative type seal, such as a tolerance fit, collar, bladder, or valve type sealing member, such as those disclosed in U.S. Pat. No. 5,490,837 to Blaeser et al., which is herein incorporated by reference. It is also recognized that distal seal member 68 may be an active seal, passive seal or combination of both.

The guide catheter shaft 20 further includes a proximal seal 70 to aid in releasably sealing the dilatation balloon assembly 18 to guide catheter 16 during inflation/deflation of balloon 48. In one embodiment, the proximal seal 70 is located proximate the proximal end of dilatation balloon system 38. Proximal seal 70 is located about the exterior periphery of proximal extension member 44. Proximal seal member 70 provides a releasable seal between the guide catheter 16 and the dilatation balloon assembly 18 (at proximal extension member 44) for allowing fluid under pressure to communicate between the lumen 26 and balloon chamber 55. In one embodiment, the proximal seal member 70 is an O-ring type seal, which prevents inflation fluid from exiting the guide catheter distal end 24. It is recognized that proximal seal 70 may be located along other parts of the dilatation balloon assembly 18 or about the interior periphery of guide catheter 16.

Proximal seal member 70 allows the dilatation balloon system 38 to releasably seal to guide catheter shaft 20 at any point along the shaft. Proximal seal member 70 may be formed of a relatively soft durometer urethane or polymeric material. In other embodiments, it is recognized that proximal seal member 70 may be an alternative type seal, such as previously disclosed herein.

The proximal extension member 44 of dilatation balloon system 38 is funnel shaped to aid in guiding guide wire 19 or other ancillary devices through dilatation balloon system 38 (in particular, through support member 40). The proximal extension member 44 of dilatation balloon system 38 includes an outward extending portion 72, an intermediate portion 74 and transition portion 76. The outside diameter of the intermediate portion 74 is proximate the inside diameter of proximal seal member 70. Outward extending portion 72 extends outward from intermediate portion 74 to contact the interior walls of the guide catheter lumen 26. The transition portion 76 extends from intermediate portion 74, and transitions from the diameter of the intermediate portion 74 to the proximal neck portion 46.

Dilatation balloon assembly 18 is passed through the lumen 26 of guide catheter 16 by operation of push member 42. Push member 42 is directed to push the dilatation balloon assembly 18 through the lumen 26 until the proximal extension member 44 (with proximal seal member 70) is positioned at the desired location proximate the guide catheter distal end 24. As push member 42 is pushed forward, the proximal seal member 70 seals the proximal extension member 44 releasably against the interior walls of guide catheter 16. During sealing, the proximal seal member 70 may be slightly deformed as the proximal extension member 44 presses outward against the proximal seal member 70 and the interior walls of guide catheter 16. Further, when the balloon 48 is inflated with inflation fluid under pressure, the outward pressure from the inflation fluid further seals the proximal extension member 44 against the proximal seal member 70. Upon removing the inflation fluid to deflate the balloon 48, the push member 42 may be operated (at its proximal end 58) to pull the dilatation balloon assembly 18 back through the lumen 26, reducing the sealing force.

Figure 1B:
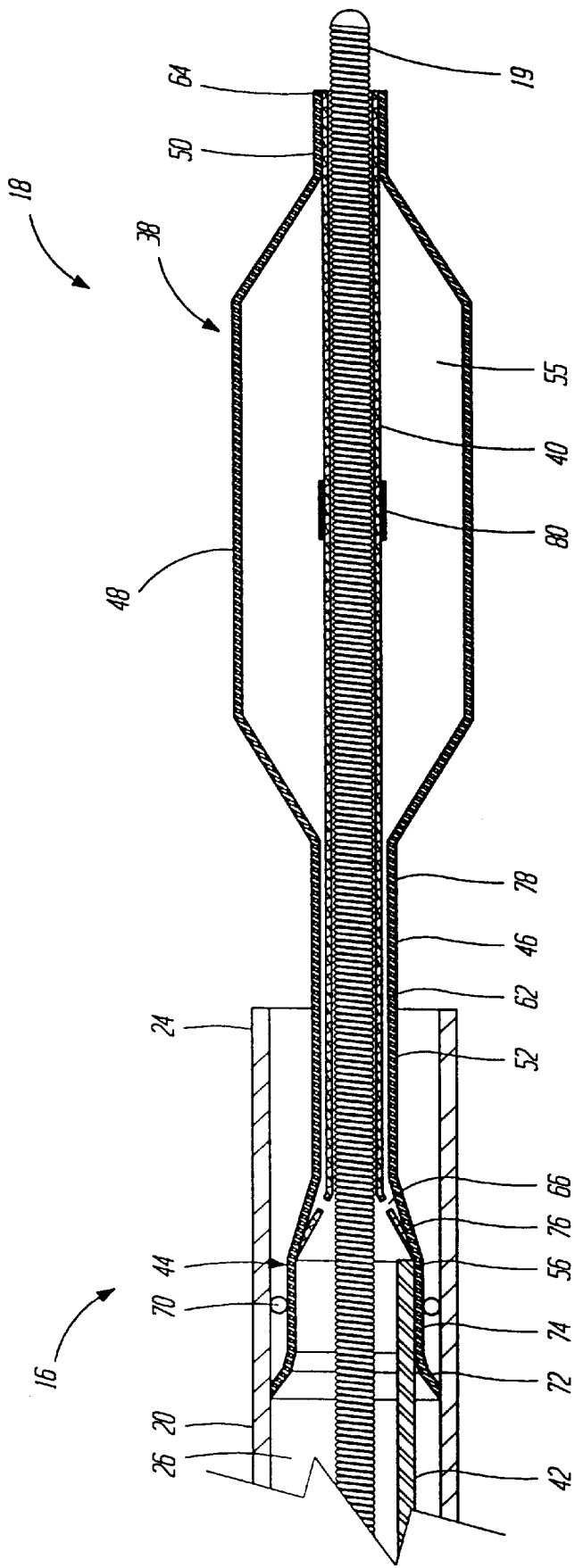
FIG. 1B is a partial longitudinal sectional view of another embodiment of the changeable distal portion of the catheter system in accordance with the present invention taken along line 1B—1B of FIG. 1.
Figure 1C:
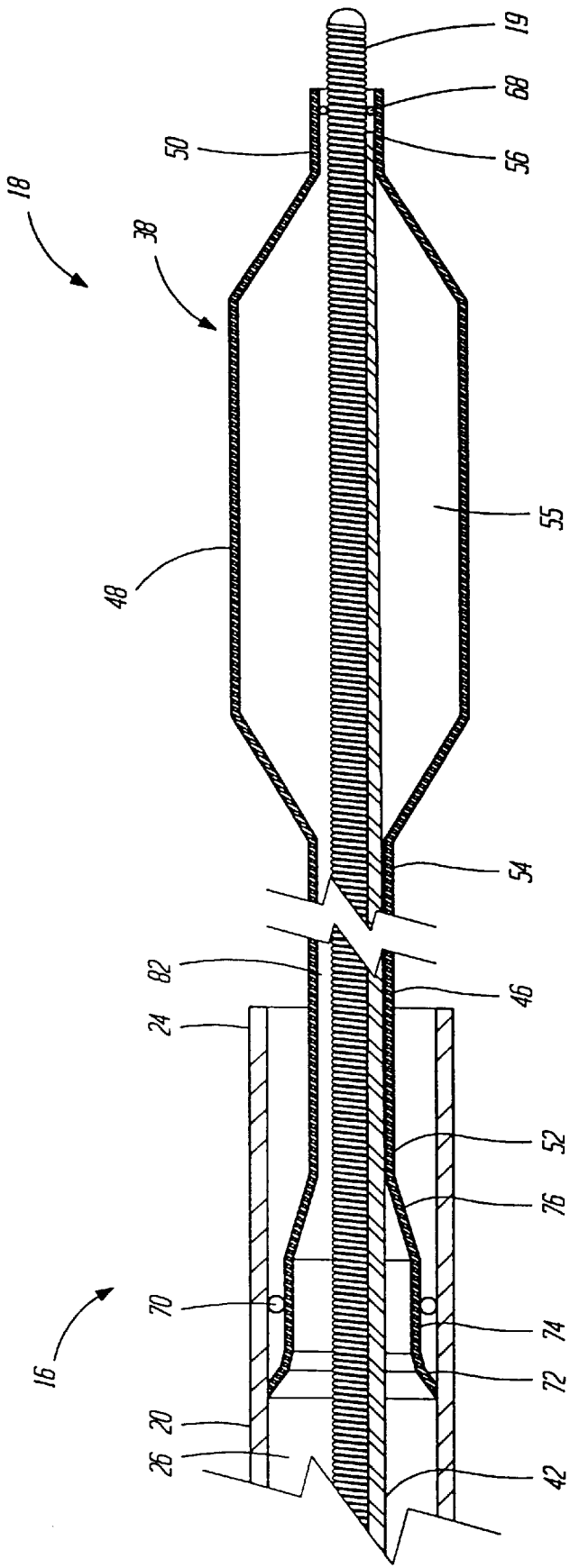
FIG. 1C is a partial longitudinal sectional view of another embodiment of the changeable distal portion of the catheter system in accordance with the present invention taken along line 1C—1C of FIG. 1.
Figure 10:
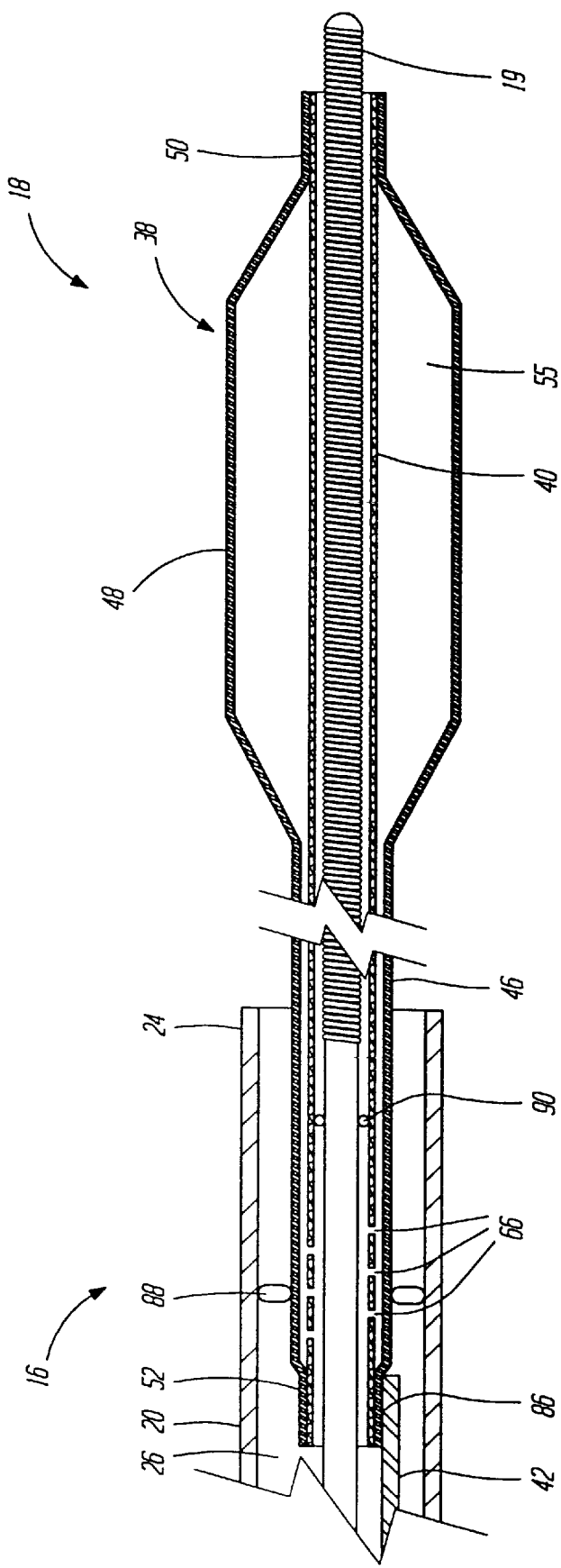

FIGS. 1B–1D illustrate alternative embodiments of the catheter assembly 10 shown in FIGS. 1 and 2. Since these embodiments can be similar to the previously described embodiment, similar parts appearing in FIGS. 1B–1D are represented by the same, corresponding reference numeral.

Referring to FIG. 1B, another embodiment of the dilatation balloon assembly 18 is generally shown. In this embodiment, support member 40 extends proximal of the proximal neck portion 46 and is secured to the proximal extension member 44 at transition portion 76. Openings 66 are located proximal of the proximal neck portion 46. The outside diameter of support member 40 along the proximal neck portion 46 is less than the inside diameter of proximal neck portion 46, creating a channel 78 extending between the openings 66 and balloon chamber 55. The outer diameter of guide wire 19 is only slightly smaller than the interior diameter of the support member 40 to create a tolerance fit which allows slidable movement of the guide wire 19 through shaft 20. When balloon 48 is inflated, the tolerance fit between the support member 40 and guide wire 19 inhibits inflation fluid from exiting the balloon 20 through support member 40.

Additionally, marker band 80 may be located along support member 40 proximate the center of balloon 48. The marker band 80 allows a physician to track the location of balloon 48 with fluoroscopy during a catheter procedure.

During inflation of balloon 48, the balloon chamber 55 is in fluid communication with the guide catheter lumen 26. In particular, fluid may pass from the lumen 26 through openings 66, through channel 78, and into balloon chamber 55.

Referring to FIG. 1C, another alternative embodiment of the dilatation balloon assembly 18 in accordance with the present invention is shown. Push member 42 extends longitudinally through the balloon chamber 55 and is secured to the balloon distal neck portion 50 and proximal neck portion 46. In one embodiment, the push member is a core wire which tapers to a smaller diameter as it passes through the dilatation balloon 38. The push member distal end 56 is secured to the interior of proximal neck portion 46 at a location proximal of distal seal member 68. Since push member 42 extends through balloon 48, the push member 42 acts as a longitudinal support to the balloon 48.

Distal seal member 68 is located about the inside periphery of distal neck portion 50, allowing guide wire 19 to pass therethrough, while inhibiting the passage of inflation fluid. Extending between the guide catheter lumen 26 and the balloon chamber 55 is a channel 82, providing fluid communication between the guide catheter 16 and balloon 48 during inflation/deflation of balloon 48.

Referring to FIG. 1D, another embodiment of the dilatation balloon assembly 18 of FIG. 1 is shown. In this embodiment, proximal neck portion 46 extends to a reduced diameter portion 86. Push member 42 is operably coupled to the outside of reduced diameter portion 86. Support member 40 extends from reduced diameter portion 86 to distal neck portion 50. Proximal end 52 has an outside diameter proximate the inside diameter of the reduced diameter portion 86, and is securely bonded to the reduced diameter portion 86 about its inside periphery at proximal end 52. The shaft distal end 90 is sealed about the inside periphery of distal neck portion 50.

The balloon catheter proximal neck portion 46 is movably/releasably sealed with guide catheter 16 along shaft 20 at proximal seal 88. The proximal seal 88 is coupled to dilatation balloon system 38. The proximal seal 88 is secured about the outside periphery of proximal neck portion 46. In one embodiment, the proximal seal 88 is an interference type, O-ring seal, having an outside diameter proximate the inside diameter of shaft 20. The proximal seal 88 may be formed of a relatively soft durometer urethane or polymeric material. In other embodiments, it is recognized that seal 88 may be an alternative type seal, such as those previously disclosed herein.

Dilatation balloon assembly 18 further includes a dilatation balloon assembly proximal seal 90 for positioning about guide wire 19 or other treatment apparatus extending therethrough. The dilatation balloon assembly proximal seal 90 may also be an O-ring type seal, and is secured about the inside periphery of support member 40. The dilatation balloon assembly proximal seal 90 allows movement of guide wire 19 relative to the dilatation balloon assembly 18, without allowing balloon inflation fluid under pressure to pass through the support member 40.

Extending through support member 40, and located proximal of dilatation balloon assembly proximal seal 90, are openings 66. The openings 66 allow fluid communication between the lumen 26 of guide catheter 16 and balloon chamber 55. Fluid under pressure is allowed to pass from lumen 26 through support member 40, through openings 66, and into the balloon interior chamber 55 of balloon 48.

With the above disclosed embodiments, the distal catheter portion 14, including dilatation balloon assembly 18, may be changed to a different shaped or sized distal catheter portion 14 while the catheter assembly 10 is positioned within a patient's vascular system, without removing the proximal catheter portion 12. Further, the proximal catheter proximal portion 12 may be sterilized for reuse in other procedures.

The present invention further includes a catheter assembly having a standard proximal portion and an interchangeable guide catheter distal portion. The interchangeable guide catheter distal portion may be provided in different sizes or shaped curves. For example, the exchangeable guide catheter distal portion may be changed out during a catheter procedure allowing a PTCA procedure to be performed in either the right or left coronary artery, without removing the proximal portion from the patient's vascular system.

Referring to FIG. 2, an application of the catheter assembly 10 in accordance with the present invention is generally shown, wherein the changeable distal portion may be a guide catheter (or diagnostic catheter). In particular, proximal catheter portion 12 is a sheath assembly or guide catheter 16, and the distal catheter portion 14, shown extending from the proximal catheter portion 12, is a guide catheter extension 102. With this application, the catheter assembly 10 allows guide catheter extension 102 to be changed during a catheter procedure to a differently sized or curved guide catheter distal portion or end. Further, the catheter assembly 10 may be insertable within a previously placed guide catheter in a patient's vascular system.

Guide catheter 16, as previously described herein, includes a shaft 20 having proximal end 22 and distal end 24, with lumen 26 (shown in FIG. 2A) extending longitudinally therethrough. Operably connected to the distal end 24 of the shaft 20 is manifold/hub assembly 28 which communicates with the lumen 26 for connection to ancillary devices (not shown) for controlling the passage of such devices and fluids therethrough. Extending from guide catheter 16 is the guide catheter extension 102.

Figure 2A:
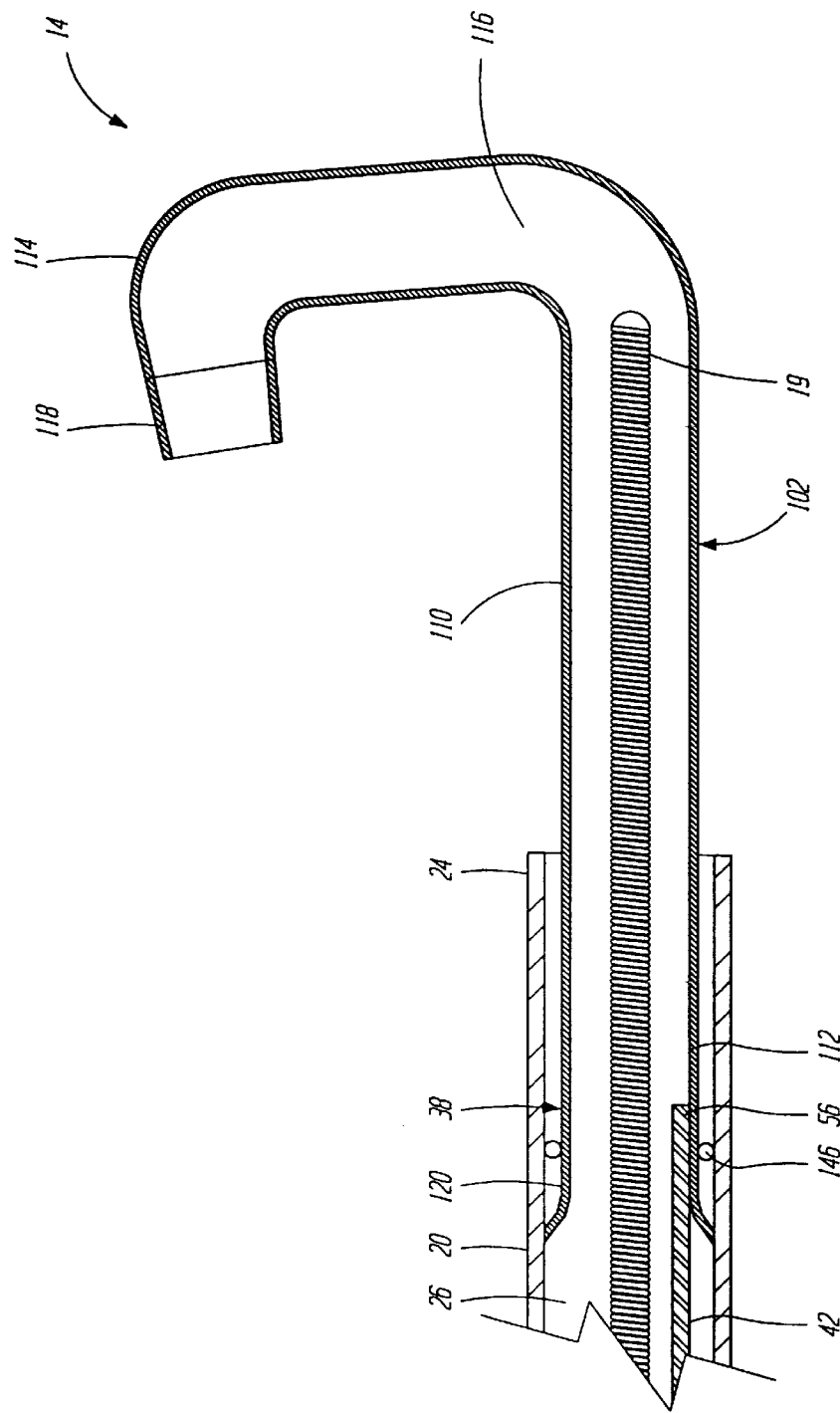
FIG. 2A is a partial longitudinal sectional view showing the changeable distal portion of the catheter system in accordance with the present invention taken along line 2A—2A of FIG. 2.

Referring to FIG. 2A, the distal portion of guide catheter extension 102 is generally shown extending from the guide catheter, in longitudinal cross-sectional view. The guide catheter extension 102 generally includes a shaft 110 having a proximal end 112 and a distal end 114. Guide catheter extension lumen 116 extends between the proximal end 112 and the distal end 114. The shaft 110 may vary in diameter, size, or be generally straight or curved. Coupled to the distal end 114 is soft tip 118. The guide catheter shaft 110 may be single or multi-layered construction, as previously described herein, and may be formed from an extrusion process. Located at the proximal end 112 is outward extending member 120. Outward extending member 120 is generally funnel shaped, and extends from a first outside diameter approximately equal to the outside diameter of guide catheter extension 110 to a second outside diameter approximately equal to the inside diameter of the guide catheter lumen 26.

The guide catheter extension 102 includes a push member 42. The push member 42 generally includes a proximal end 50 and a distal end 56 (as previously described herein). The push member 42 is operably coupled to the shaft 110 proximate outwardly extending member 120 proximate its distal end 56.

Guide catheter extension 102 includes a distal seal member 146 located proximate its proximal end 112. In one embodiment, the distal seal member 146 is an O-ring seal formed of a relatively soft durometer urethane or polymeric material, as previously described herein. The distal seal member 146 extends about the entire exterior periphery of guide catheter extension 102. Preferably, the inner diameter of lumen 26 is proximate the outer diameter of the distal seal member 146 to create an interference seal which allows slidable movement of the shaft 110 relative to the seal member 146. Distal seal member 146 allows a releasable seal to be made at any location along the guide catheter shaft 20. It is recognized that the distal seal member 146 may be an alternative type seal, such as those previously described herein.

To seal/engage the guide catheter extension 102 to guide catheter 16 at a desired location, push member 42 is operated from a location proximal manifold 28 to push the guide catheter extension 102 through the guide catheter lumen 26 until the outwardly extending member 120 is located proximate the guide catheter shaft distal end 24. As push member 142 is pushed forward to the desired location, guide catheter seal member 146 provides a fluid tight seal between the guide catheter extension 102 and guide catheter 16. To change the catheter extension 102 to a different size or different curved guide catheter extension, the push member 42 is operated from a location proximal manifold 28 to pull the shaft 110 back through the lumen 26, releasing the seal between the guide catheter seal member 146 and the guide catheter shaft 20. Similarly, a second guide catheter extension 102 may be inserted into the shaft lumen 26 and operably positioned as previously described herein.

Figure 3:
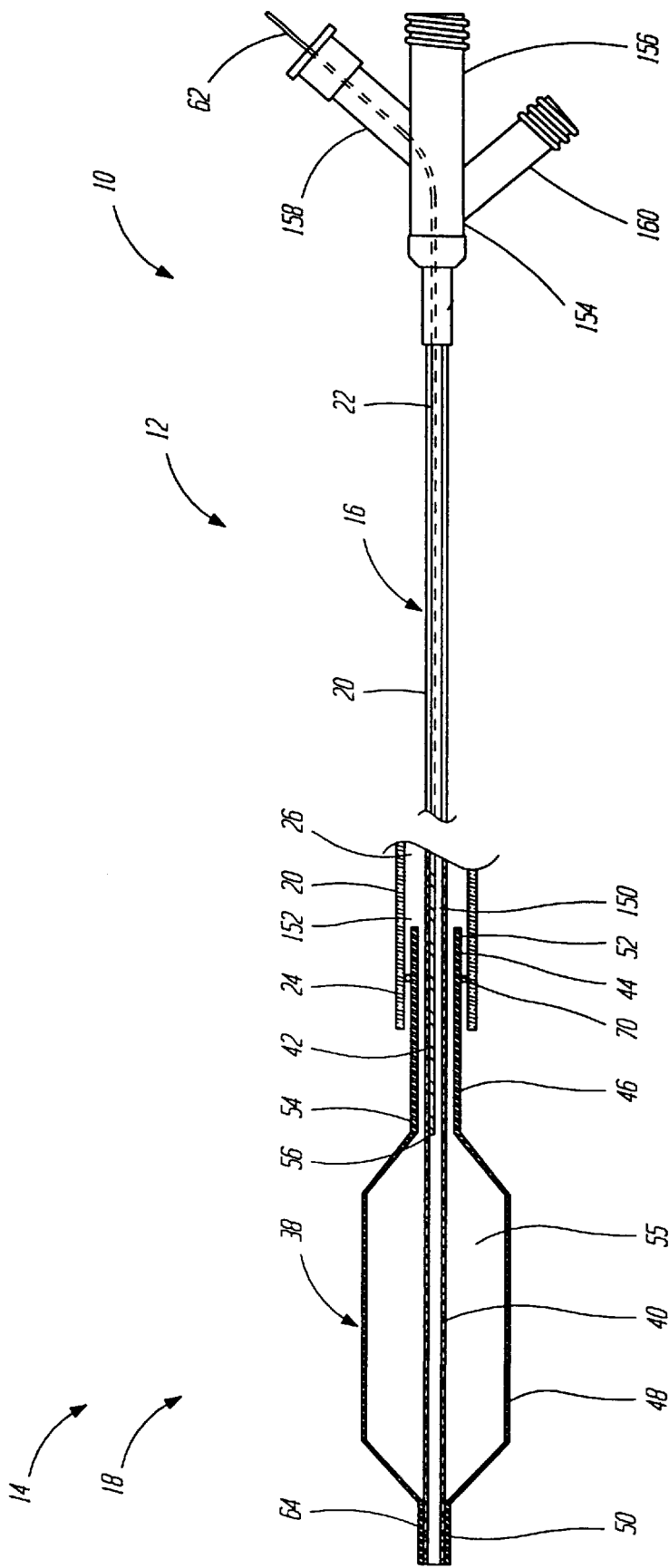
FIG. 3 is a side view of another embodiment of a catheter system having a changeable distal portion in accordance with the present invention, having a dual lumen design.

Referring to FIG. 3, another application of the catheter assembly 10 in accordance with the present invention is generally shown. In this embodiment, the catheter assembly 10 is a co-axial lumen catheter assembly. Proximal catheter portion 12 is a coaxial catheter assembly, and the distal catheter portion 14, shown in an enlarged cross-sectional longitudinal view, is dilatation balloon assembly 18. The unique embodiment in accordance with the present invention provides for a co-axial lumen design, wherein the changeable distal catheter portion 14 may be releasably coupled to the proximal catheter portion 12, and may be exchanged during a catheter procedure while the proximal catheter portion 12 is positioned in a patient's vascular system. Catheter assembly 10 may be insertable in a guide catheter previously placed within a patient's vascular system.

The catheter assembly 10 co-axial lumen design includes guide catheter lumen 26 divided into an inner lumen 150 and an outer lumen 152. The inner lumen 150 allows contrast media, guide wire 19, and/or treatment devices to pass therethrough, isolated from outer lumen 152. Outer lumen 152 is in fluid communication with balloon chamber 55 for inflation/deflation of balloon 48.

Coupled to the proximal end 22 of shaft 20 is a Y-adapter 154 having a central port 156, side port 158, and a side port 160. The inner lumen 150 is the interior lumen of support member or shaft 40. Inner lumen 150 extends longitudinally between the balloon assembly distal neck portion 50 and the Y-adapter 154.

The support member 40 distal portion 64 is sealed about the interior periphery of the balloon assembly distal neck portion 50. support member 40 extends through the balloon chamber 55 and proximal neck portion 46, through lumen 26, exiting Y-adapter side port 158. Support member 40 may be used as a push member for positioning/movement of dilatation balloon 38 relative to guide catheter shaft 20, from a location proximal Y-adapter 154. Further, push member 42 may be positioned within inner lumen 150. In one embodiment, push member distal end 56 is secured to the interior of support member 40 at a location proximate the balloon 48. Push member 42 extends through the inner lumen 150 of support member 40 and exits side port 158 of the Y-adapter 154. Inner lumen 150 may be used for passing a guide wire therethrough. Since support member 40 extends the full length of catheter assembly 10 and may be isolated from the inflation lumen, the need for a guide wire seal as previously described herein is eliminated.

Proximal seal member 70 is located proximate the proximal neck portion 46 proximal end 52. Proximal seal member 70 provides a fluid-tight releasable seal between the dilatation balloon proximal neck portion 46 and the guide catheter shaft 20. In one embodiment, the proximal seal member 70 is an O-ring seal formed of a relatively soft durometer urethane or polymeric material, or as previously disclosed herein. The proximal seal member 70 extends about the entire exterior periphery of proximal neck portion 46. Proximal seal member 70 is an interference type seal. Preferably, the outer diameter of proximal seal member 70 is proximate the inner diameter of shaft 20 to create a fluid-tight interference seal which allows slidable movement of the dilatation balloon system 38 relative to the guide catheter shaft 20. When balloon 48 is inflated with fluid, the interference fit between the proximal seal member 70 and the shaft 20 inhibits inflation fluid from exiting the balloon 48 through the shaft distal end 24. In other embodiments, it is recognized that proximal seal member 70 may be an alternative type seal as previously described herein.

Proximal seal member 70 provides a releasable seal between guide catheter 16 and the dilatation balloon assembly proximal neck portion 46 for allowing fluid under pressure to communicate between outer lumen 152 and balloon chamber 55 through the proximal neck portion 46.

Dilatation balloon assembly 18 is moved through the Y-adapter 154 (port 158) and through lumen 26 of guide catheter 16 by operation of push member 42 (and/or support member 40). Push member 42 is directed to push the dilatation balloon assembly 18 through lumen 26 until the proximal seal member 70 is positioned at a desired location proximate the shaft distal end 24. As push member 42 is pushed forward, the proximal seal member 70 is sealed against the interior walls of guide catheter 16.

Outer lumen 152 is in fluid communication with balloon chamber 55 for inflation/deflation of balloon 48. Inner lumen 150 may be used as a guide wire lumen, for the injection of contrast media, or for the passage of other treatment devices through the catheter assembly 10. Upon removing the inflation fluid to deflate the balloon 48, the push member 42 may be operated at its proximal end 58 to pull the dilatation balloon assembly 18 back through lumen 26, lessening (reducing) the seal pressure between the dilatation balloon assembly 18 and the guide catheter 16.

In operation of the catheter assembly 10, intravascular access is initially made in a conventional manner. For use in an angioplasty procedure, the patient's femoral artery is entered percutaneously and a sheath is inserted for access to the vascular system. Although the angioplasty procedure described herein utilizing the femoral artery to access the patient's vascular system is the most common method, it is also recognized that the present invention may be used for brachial and radial artery access using similar procedures. It is also recognized that the present invention may be used in non-coronary procedures, such as PTA, cerebral or other non-vascular procedures.

To initially position the catheter assembly 10 in a patient's vascular system, a guide catheter placement guide wire is preferably inserted into lumen 26 while the entire guide catheter 16 is outside the body, such that the distal tip of the guide wire extends beyond the guide catheter 16. The combination of the guide catheter 16 and the guide wire is then advanced to a desired location in the vascular system, in particular, it is advanced through the femoral artery and up over the aortic arch. The guide wire may be inserted into the vessel prior to advancement of the guide catheter 16 over the guide wire, or the guide catheter 16 can be inserted into the vessel prior to advancement of the guide wire through lumen 26. The guide catheter placement guide wire is removed and guide wire 19 is inserted into the guide catheter 16 and advanced until the guide wire 19 distal end is located proximate the guide catheter distal end 24. Alternatively, it is recognized that catheter assembly 10 may be inserted within a previously placed guide catheter in a patient's vascular system.

The catheter assembly 10 may be advanced to seat or deep seat the guide catheter 16 soft tip 30 in the ostium of the coronary to receivestreatment. The guide wire 19 may further be advanced beyond the guide catheter distal end 24 and positioned across the stenosis receiving treatment.

Once a path across the stenosis has been established, the dilatation balloon assembly 18 may be back loaded onto the guide wire 19, and passed through the guide catheter 16, tracking the guide wire 19 into the coronary artery receiving treatment. The dilatation balloon assembly 18 is advanced through the guide catheter 16 by operation of the push member 42 from a location proximal of the guide catheter 16, outside of the patient's body.

The push member 42 is directed to push the dilatation balloon assembly 18 through the guide catheter lumen 26 until the proximal seal member 70 is located at the desired location (proximate guide catheter distal end 24). As push member 42 is pushed forward, the proximal seal member 70 is sealed (fluid tight) against the interior walls of guide catheter 16. During sealing, the proximal seal member 70 may be slightly deformed as the proximal seal member 70 pushes against the interior walls of guide catheter 16.

The balloon 48 tracks the guide wire 19 and is positioned across the stenosis. When the balloon 48 is inflated with inflation fluid under pressure for treatment of the stenosis, the outward pressure from the inflation fluid further seals the proximal seal member 70 against the shaft 20. Upon completion of treatment using balloon 48, inflation fluid is removed to deflate the balloon 48, and the push member 42 may be operated (at its proximal end 58) to pull the dilatation balloon assembly 18 back through the lumen 26, releasing the seal between the proximal extension member 44 and guide catheter 16.

If a different size or configuration dilatation balloon assembly 18 is required for treatment of the stenosis, the dilatation balloon assembly 18 may be withdrawn back through the guide catheter 16 at lumen 26. The guide wire 19 remains stationary within the vascular system for maintaining the path across the patient's stenosis. A second or different dilatation balloon assembly 18 may now be back loaded onto the guide wire 19 and tracked through the guide catheter lumen 26 until it is similarly sealingly engaged at a desired location proximate the guide catheter distal end 24. The balloon 48 may now be positioned for further treatment of the stenosis.

If, during treatment, it is desired to inject contrast media into the patient's vascular system, the balloon 48 may be deflated, and the push member 42 may be operated (at its proximal end 58) to pull the dilatation balloon assembly 18 back into the guide catheter lumen 26, releasing or disengaging the seal between the proximal seal portion and the guide catheter 16. Once the dilatation balloon assembly 18 is pulled back to a location proximal a sealing position of the guide catheter proximal seal member 70 (or withdrawn totally from guide catheter lumen 26), contrast medium may be injected through lumen 26 and into the patient's vascular system. Upon completion of the injection of contrast medium, the push member 42 may again be operated at its proximal end to push the dilatation balloon assembly 18 until the dilatation balloon assembly 18 is resealed against the interior walls of guide catheter 16 at proximal seal member 70 at a desired location.

The unique present invention allows the changeable distal catheter portion 14 to be resealably connected to the proximal catheter portion 12, allowing for balloon inflation/deflation and easy exchange of the distal catheter portion 18 during a catheter procedure. Further, the proximal catheter portion 12 may be resterilized and reused with other distal catheter portions 14 in future procedures.

In a similar manner, sheath or guide catheter 16 may be positioned within a patient's vascular system, having guide wire 19 passing therethrough. A desired guide catheter extension 102 is selected, and push member 42 is operated from a location proximal manifold 28 to push the guide catheter extension 102 through the sheath lumen 26 until the sheath seal member 146 is positioned at a desired location proximate the guide catheter distal end 24. As push member 42 is pushed forward, the sheath seal member 146 engages the shaft 20 providing a fluid tight seal of the catheter assembly 102 against guide catheter 16. If it is desired to change out the catheter extension 102 to a different size or different curved guide catheter extension, the push member 42 is operated from a location proximal manifold 28 to pull the shaft 110 back through lumen 26, releasing the seal between the sheath seal member 146 and the guide catheter shaft 20. The guide wire 19 remains stationary within the vascular system to maintain a desired treatment path. A second or different guide catheter extension 102 may now be back loaded onto the guide wire 19 and tracked through the sheath lumen 26 until it is similarly sealingly engaged at a desired location against guide catheter 26. It is recognized that it is not necessary to have a guide wire 19 in place for positioning and exchanging guide catheter extension 102, since guide catheter extension 102 is operably controlled from a location proximal of guide catheter 16 using push member 42. Once access to a desired coronary region is established using guide catheter extension 102, a desired treatment device may be tracked through the sheath lumen 26 for treatment of the diseased coronary region.

Although the present invention has been described with reference to preferred embodiments, those skilled in the art will recognize that changes may be made in form and detail without departing from the spirit and scope of the invention. For example, it is recognized that catheter assembly 10 may be inserted within a guide catheter placed within a patient's vascular system, or alternatively, catheter assembly 10 may be used without an additional guide catheter. Additionally, it is recognized that push member 42 may be in the form of a core wire, a rod, or a tubular member. As such, it is intended that the foregoing detailed description be regarded as illustrative, rather than limiting that it is the following claims, including all equivalents thereof, which are intended to define the scope of the invention.

What is claimed is:

1. A catheter assembly having a co-axial lumen design comprising:
   a proximal shaft section having a proximal end, a distal end, and a proximal shaft lumen extending therethrough;
   a distal assembly insertable within the proximal shaft lumen including a distal shaft section having a proximal end, a distal end, a distal lumen extending therethrough, a balloon carried proximate the distal shaft section in fluid communication with the distal lumen;
   a releasable seal coupled to the distal shaft for releasably sealing the proximal shaft lumen in fluid communication with the distal lumen during a catheter procedure; and
   a support shaft extending through the proximal shaft lumen, the distal lumen, and the balloon, having a proximal end, a distal end, and a lumen extending therethrough, wherein the distal end is sealed go proximate a distal end of the balloon.

2. The catheter assembly of claim 1, wherein the support shaft has an outside diameter less than the diameter of the distal lumen allowing fluid communication between the proximal shaft lumen and the balloon.

3. The catheter assembly of claim 1, wherein the releasable seal is an interference seal secured about the exterior periphery of the distal shaft section.

4. The catheter assembly of claim 1, further comprising a push member operably coupled proximate the distal end of the support shaft.

5. The catheter assembly of claim 1, wherein the support shaft lumen is a guide wire lumen.

6. The catheter assembly of claim 1, wherein the support shaft lumen is isolated from the proximal shaft lumen.

7. A catheter assembly, comprising:
   a proximal outer shaft having a proximal end, a distal end, and a proximal shaft lumen extending therethrough;
   a distal assembly having a distal outer shaft, wherein the distal outer shaft has a proximal end, a distal end, and a distal shaft lumen extending therethrough, the distal outer shaft being slidable with respect to the proximal outer shaft;
   a seal interposed between the distal outer shaft and the proximal outer shaft for forming a seal therebetween; and
   an inner shaft having an inner lumen extending therethrough, the inner shaft operably attached to the distal assembly and positioned within at least a portion of the distal shaft lumen.

8. A catheter according to claim 7 wherein the cross-sectional area of the inner shaft is less than the cross-scctional area of the distal outer shaft, thereby forming an inflation lumen therebetween.

9. A catheter according to claim 8 wherein the distal assembly further includes a balloon having a balloon interior, wherein the balloon interior is in fluid communication with the inflation lumen.

10. A catheter according to claim 9 wherein the balloon has a proximal neck and a distal neck, the proximal neck being operably attached to the distal outer shaft and the distal neck being operably attached to the inner shaft.

11. A catheter according to claim 7 wherein the inner shaft extends to the proximal end of the proximal outer shaft.

12. A catheter according to claim 7 wherein the inner lumen is a guide wire lumen.

13. A catheter according to claim 7 further comprising a push member operably attached to the distal assembly.

14. A catheter according to claim 13 wherein the push member extends to the proximal end of the proximal outer shaft.

15. A catheter according to claim 7 wherein the seal is of a type selected from the group consisting of an interference type seal, a collar type seal, a bladder type seal and a valve type seal.

16. A catheter according to claim 7 wherein the distal outer shaft is slidably received by the proximal shaft lumen of the proximal outer shaft.

17. A method for exchanging a first distal portion for a second distal portion of a catheter, wherein the catheter has a distal portion that is in a slidable relationship with a proximal portion, the method comprising the steps of:
   sliding the first distal portion proximally of the proximal end of the proximal portion; and
   sliding the second distal portion distally along the proximal portion until the proximal end of the second distal portion is proximate the distal end of the proximal portion.

* * * * *

UNITED STATES PATENT AND TRADEMARK OFFICE
CERTIFICATE OF CORRECTION

PATENT NO. : 5,941,871
DATED      : August 24, 1999
INVENTOR(S): Daniel O. Adams et al.

It is certified that error appears in the above-identified patent and that said Letters Patent is hereby corrected as shown below:

Column 13, line 26, delete "go".

Signed and Sealed this

Twenty-third Day of May, 2000

Attest:

Q. TODD DICKINSON

*Attesting Officer*       *Director of Patents and Trademarks*